United States Patent [19]

Ogura et al.

[11] Patent Number: 4,592,237

[45] Date of Patent: Jun. 3, 1986

[54] METHOD OF SELECTING COMPOSITE RECEPTION SIGNAL IN ULTRASONIC INSPECTION APPARATUS AND APPARATUS THEREFOR

[75] Inventors: Satoshi Ogura, Hitachi; Sakae Sugiyama, Ibaraki; Kazunori Koga, Hitachi, all of Japan

[73] Assignee: Hitachi, Ltd., Tokyo, Japan

[21] Appl. No.: 609,834

[22] Filed: May 14, 1984

[30] Foreign Application Priority Data

May 12, 1983 [JP] Japan .................................. 58-81797

[51] Int. Cl.⁴ ............................................. G01N 29/04
[52] U.S. Cl. ........................................ 73/602; 73/609; 73/628
[58] Field of Search ................. 73/602, 609, 626, 628, 73/641

[56] References Cited

U.S. PATENT DOCUMENTS 4,173,007 10/1979 McKeighen et al. .................. 73/609
4,228,686 10/1980 Tancrell .................................. 73/626
4,267,584 5/1981 McKeighen et al. .................. 73/609
4,434,658 3/1984 Miyazaki et al. ...................... 73/626

Primary Examiner—Anthony V. Ciarlante
Attorney, Agent, or Firm—Antonelli, Terry & Wands

[57] ABSTRACT

An ultrasonic flaw detecting technique in which reflection echoes of ultrasonic waves transmitted from a plurality of vibrator elements are received, and a composite signal obtained by composing the reception signals is supplied to a composite signal reception processing circuit. A method and an apparatus in which the existence of the composite signal is detected at a first time point at which the composite signal based on the reflection echoes from an inspection target in a main lobe can be detected and at a second and a third time point which are in advance of and later than the first time point respectively and at which the composite signal based on the reflection echoes from an inspection target in the main lobe can not be detected, so that when the existence of the composite signal is detected only at the first time point, it is determined that the composite signal is that based on the reflection echoes from the inspection target.

6 Claims, 15 Drawing Figures

WAVE COMPOSITION AT FOCAL POINT F AND COMPOSITE RECEPTION WAVE

WAVE COMPOSITION AT PSEUDE FOCAL POINT F' AND COMPOSITE RECEPTION WAVE

FIG. 3a
PRIOR ART
FIG. 3b
PRIOR ART
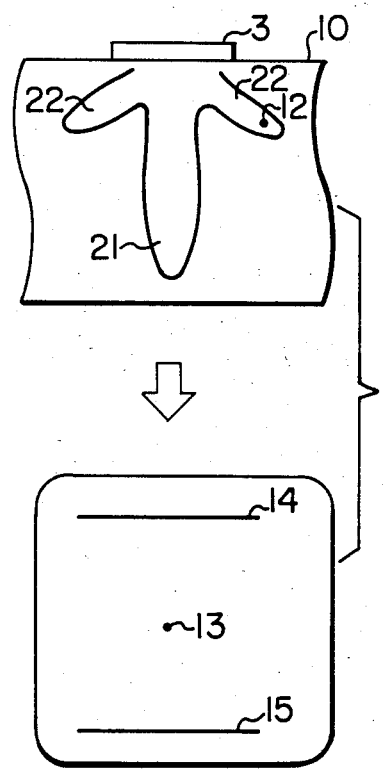
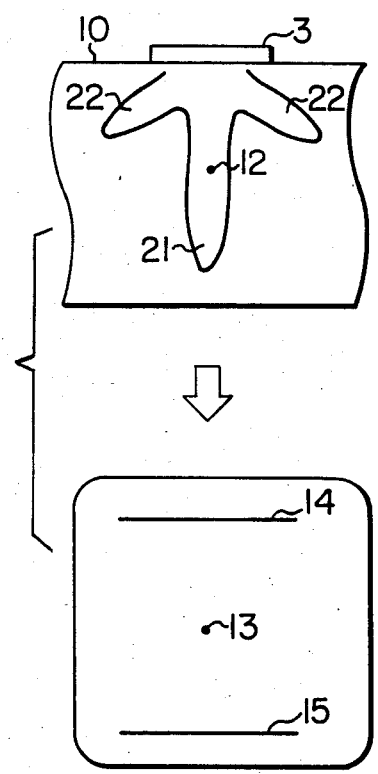

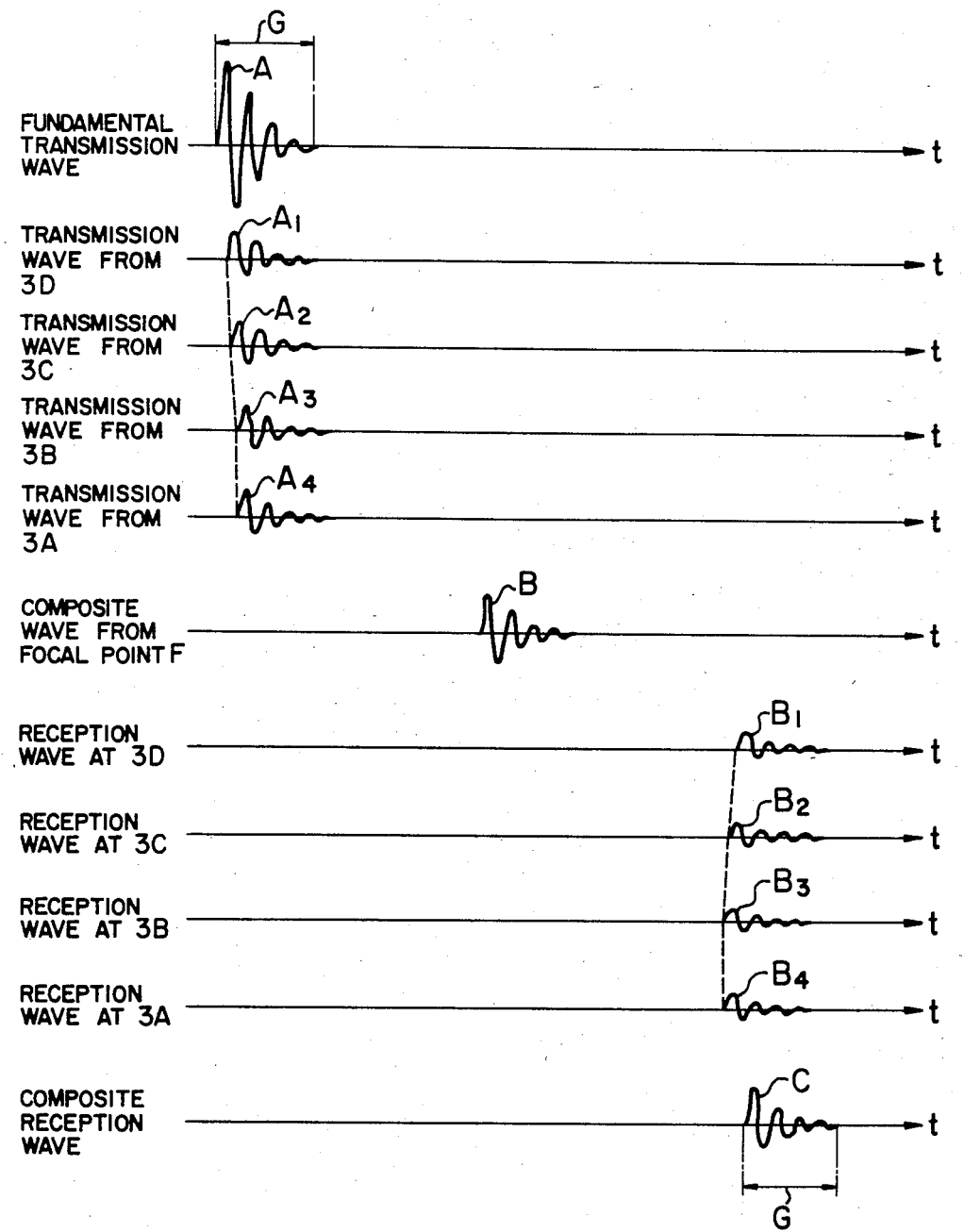

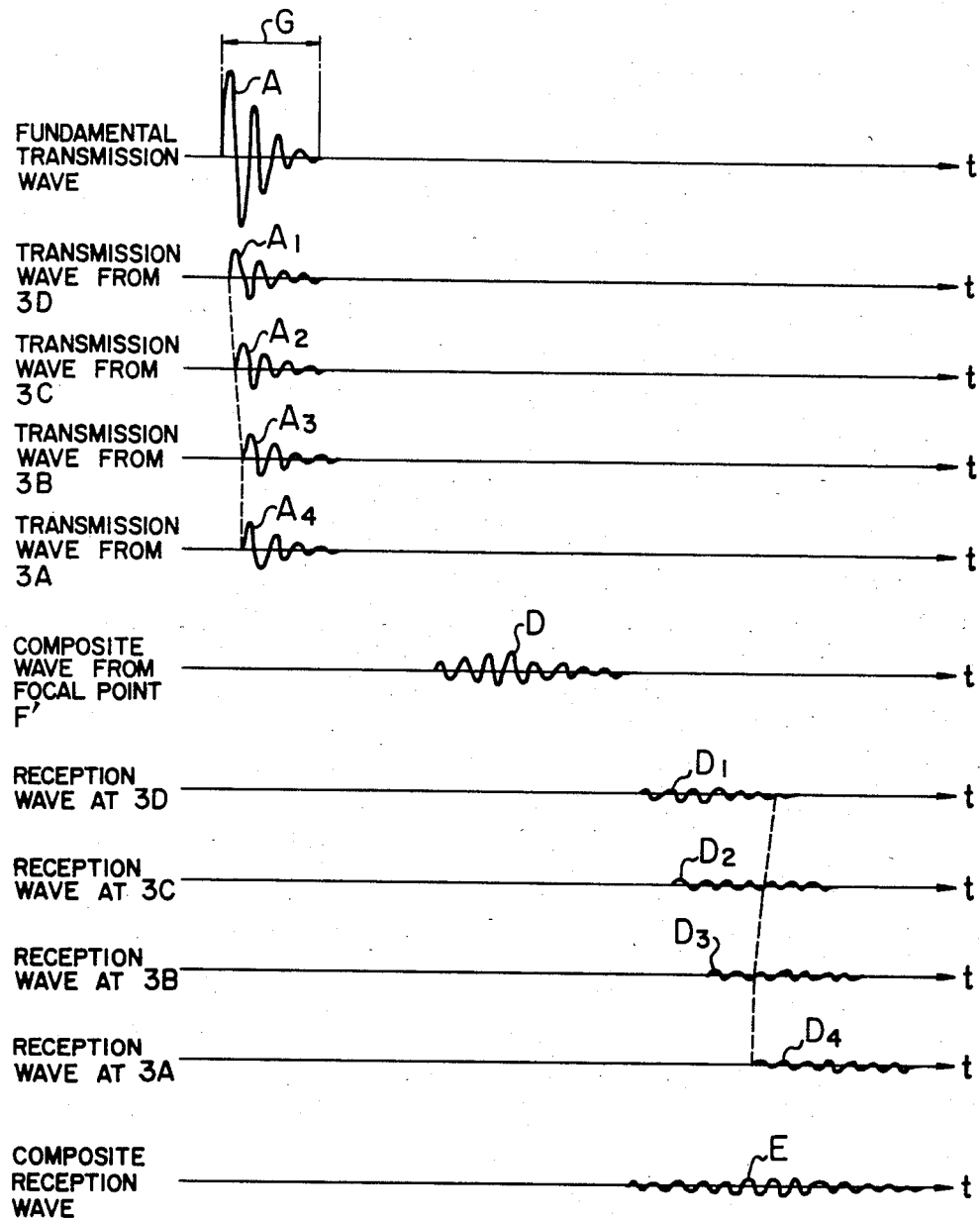

METHOD OF SELECTING COMPOSITE RECEPTION SIGNAL IN ULTRASONIC INSPECTION APPARATUS AND APPARATUS THEREFOR

The present invention relates to an ultrasonic flaw detecting technique and particularly includes a technique in which ultrasonic waves are generated from a plurality of vibrator elements with delay time factors, the reflection echoes of the ultrasonic waves are received, the received signals are composed with the delay time factors, and judgement is made as to whether the composite signal is a composite signal based on the reception signals from the focal area in the main lobe or not.

An ultrasonic inspection apparatus for inspecting the inside of an object to be inspected or a test piece by using a plurality of ultrasonic vibrator elements is known, for example, by U.S. Pat. No. 4,173,007 and Japanese Patent Application Laid-open No. 211061/1982.

According to these prior art examples, the ultrasonic wave transmission timings of the respective vibrator elements are controlled through delay means so that it is made possible to attain a state in which the acoustic pressure distribution of the acoustic waves transmitted from the vibrator elements toward the test piece is collected or focused onto the inspection target position and to perform the scanning to displace the focal point.

A probe composed of a plurality of ultrasonic vibrator elements is called an array probe or array sensor.

Combining this array probe with delay means, as described above, it is made possible to higher the acoustic pressure at the inspection target position to increase the intensity of the reflection echo from the inspection target position.

If ultrasonic waves are transmitted by the array probe, however, a grating lobe or side lobe is generated in addition to a main lobe containing therein the inspection target position. Therefore, even if an ultrasonic reflection echo is obtained, it is difficult to judge whether the reflection echo is based on the main lobe or grating lobe, so that there is a risk of erroneous position evaluation of a reflector in a test piece. Although it is necessary to judge whether the reflection echo is based on the main lobe or grating lobe in order to make certain of the position evaluation, it is not possible to cope with this requirement in the existing circumstances.

The above-mentioned circumstances may be described as follows:

FIG. 1 shows the outline of the electronically-scanning type ultrasonic inspection apparatus together with a test piece, in the case where sector scanning is performed by an array probe. In this arrangement, a high tension impulse from a pulser 1 is applied to a plurality of vibrator elements (four in number in this example) constituting an array probe 3. If the timings of application of the impulses to the respective vibrators are suitably controlled by delay elements 2 each being provided with a controllable delay time, the ultrasonic waves transmitted from the respective vibrator elements to a test piece 10 are focused in the state of superposition and can be deflected. Although each delay time is controlled such that the ultrasonic waves are focused at a focal point F in the example of FIG. 1, it is a matter of course that the ultrasonic waves can be focused at a desired point other than F. If any reflector such as a flaw exists in the test piece 10, the ultrasonic echoes from the flaw are made to be in phase through the vibrator elements and the delay elements 2, and then supplied through an adder to a signal processor 37 so as to be processed therein.

FIG. 2 shows, by constant-acoustic-pressure level lines, an acoustic pressure distribution of ultrasonic beam produced by an array probe with a focus of 50 mm and disposed at a position 0 mm. As seen in the drawing, other than a main lobe 21 to be used for inspection, a grating lobe 22 can be generated in the direction different from that of the main lobe 21. In FIG. 2, numerals 0.1, 0.2, ... represent the acoustic pressure level. Due to the existence of this grating lobe, it is made difficult to easily judge whether ultrasonic echoes are caused by a flaw existing in the main lobe or by a flaw existing in the grating lobe even if the ultrasonic echoes are received. This judgement is made difficult also by the fact that the direction of the grating lobe varies depending on the difference of acoustic velocity in the test piece. In either event, the existence of the grating lobe provides a cause of errors in positional evaluation for a reflector such as a flaw in the piece. FIGS. 3a and 3b show particular examples of the judgement. A reflector 12 exists in the grating lobe 22 in the example of FIG. 3a and in the main lobe 21 in the example FIG. 3b, while substantially in the same position in both the examples in view of the ultrasonic wave propagation time, so that ultrasonic waves can be obtained in the same timing in both the examples and it is made difficult to detect any difference between the displayed positions of the reflector images 13 and 13 on the respective displays. Reference numerals 14 and 15 represent an image of the top surface and an image of the bottom surface respectively.

The mechanism of generating such a grating lobe will be now described.

FIG. 4 shows the state of acoustic pressure level in the test piece 10 when the same first delay time is given to each of the vibrator elements 3A and 3B, a second delay time which is slightly delayed from the first one is given to the vibrator element 3C, and a third delay time which is slightly delayed from the second delay time is given to the vibrator element 3D. In the drawing, it will be appreciated that a pseudo focal point F' can be formed in addition to the desired focal point F. In this pseudo focal point F', the ultrasonic waves are superposed in the state that the wavelengths of the respective waves are shifted by an integer multiple to form a portion of high acoustic pressure level, resulting in the formation of a grating lobe.

An object of the present invention is therefore to provide a method of transmitting/receiving ultrasonic waves and an apparatus therefor.

According to an aspect of the present invention, the ultrasonic inspection method in which ultrasonic waves respectively transmitted from a plurality of vibrator means are reflected by a reflector in a test piece to produce reflection waves and the reflection waves are received as reception signals which are composed into a composite signal, comprises the steps of: detecting the existence of a composite signal based on the reflection waves from a focal point in a main lobe at each of at least a first time point at which the composite signal can be detected, a second and a third time point in the vicinity of the first time point at which the composite signal can not be detected; and deciding that the composite signal is based on the reflection waves from a position of inspection target when the existence of the composite signal is detected only at the first time point.

According to another aspect of the present invention, the ultrasonic inspection apparatus comprising a plurality of vibrator means, composing means for receiving respective output signals of the plurality of vibrator means to compose the output signals to thereby produce an output, and signal processing means for receiving the output of the composite means, further comprises a time gate circuit including: a plurality of detection means which are arranged to receive the output of the composite means and detecting operation time points of which are set to a time point at which a composite signal based on the reflection waves from a focal point in a main lobe can be detected and a time point at which the composite signal can not be detected; and a judgement circuit connected to the respective outputs of the plurality of detection means and for judging a state in which a part of the plurality of detection means detect the composite signal while the remainder of the plurality of detection means can not detect the composite signal.

The present invention will be apparent from the following detailed description taken in conjunction with the accompanying drawings, in which:

FIG. 3a is a schematic diagram showing a prior art example of the relation between the position of reflector in the grating lobe and the displaying state by a display;

FIG. 3b is a schematic diagram showing a prior art example of the relation between the position of reflector in the main lobe and the displaying state by a display;

FIG. 5 is an explanatory diagram showing the principle of the present invention in which shown is the relation among the transmission, reception and composite signals with respect to the lapse of time in the case where a reflector exists in the focal area in the main lobe;

FIG. 6 is an explanatory diagram showing the principle of the present invention in which shown is the relation among the transmission, reception and composite signals with respect to the lapse of time in the case where a reflector exists in the pseudo focal area in the grating lobe;

Figure 1:
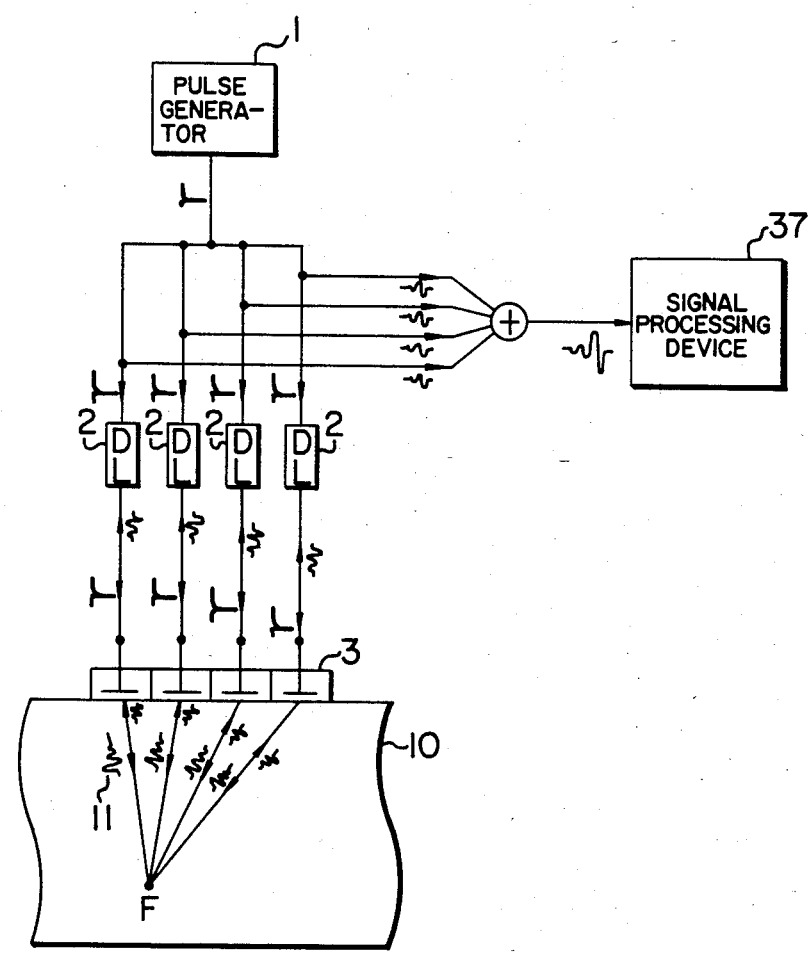
FIG. 1 is a schematic diagram showing the outline of a prior art example of electronically-scanning type ultrasonic inspection apparatus provided with an array probe, together with a test piece.
Figure 2:
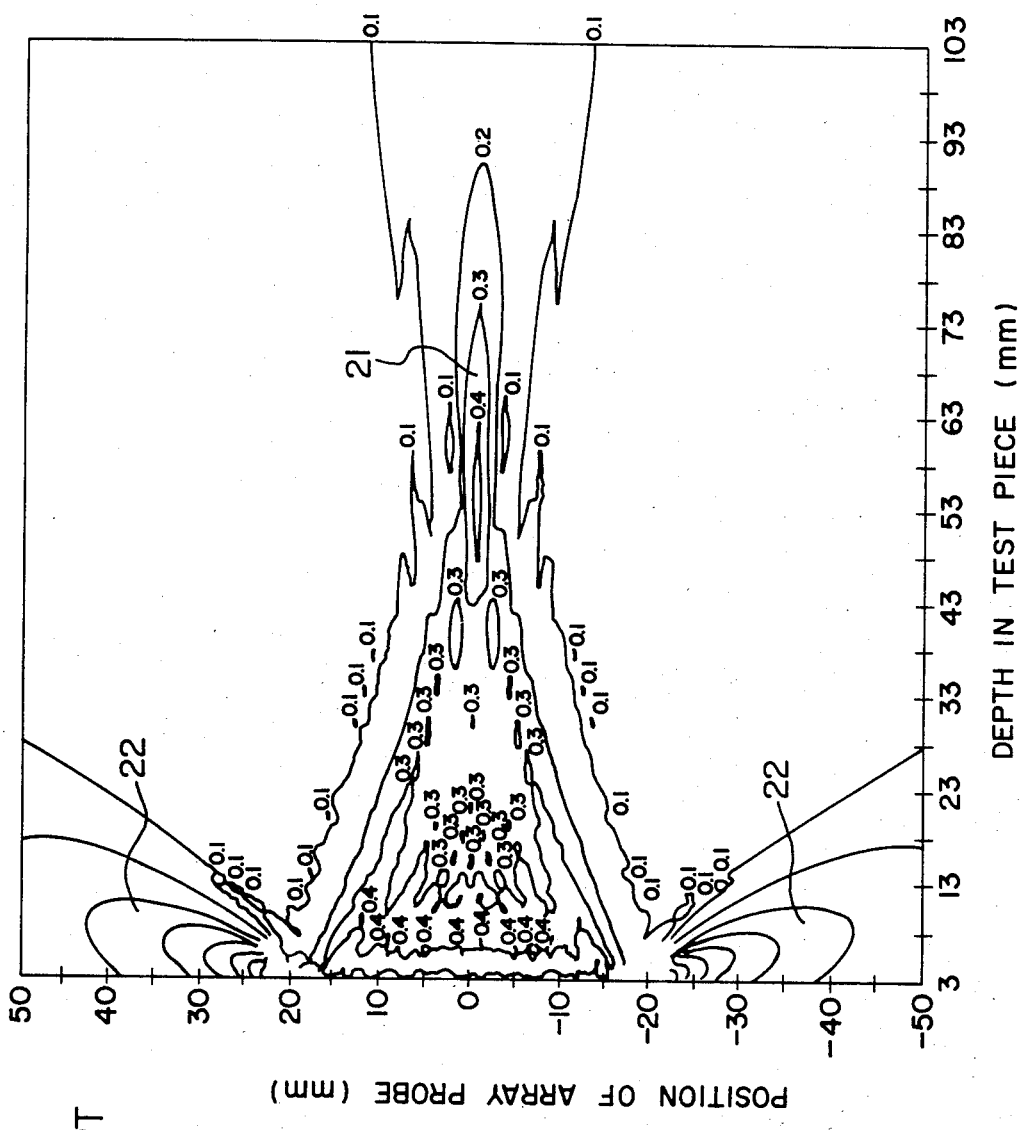
FIG. 2 is a diagram showing a prior art example of acoustic pressure distribution in the test piece due to the ultrasonic waves from the array probe.
Figure 4:
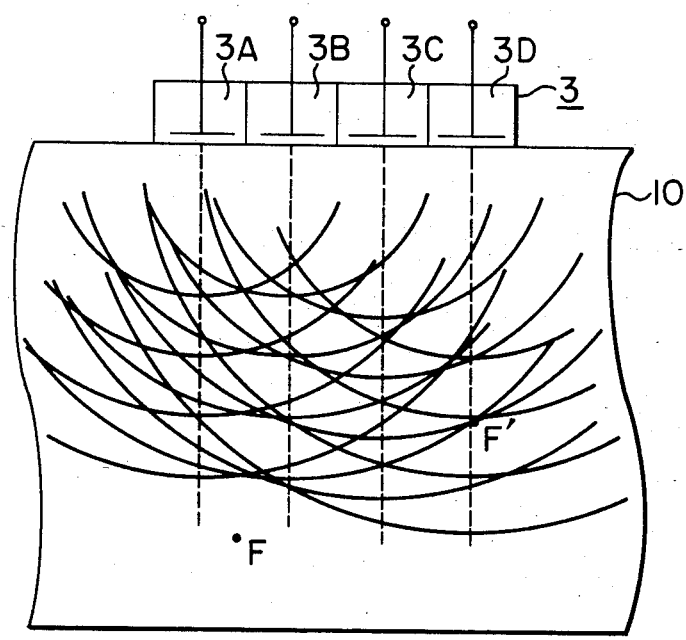
FIG. 4 is a schematic diagram showing a prior art example of the superposition of acoustic waves from the respective ultrasonic vibrators.
Figure 7A:
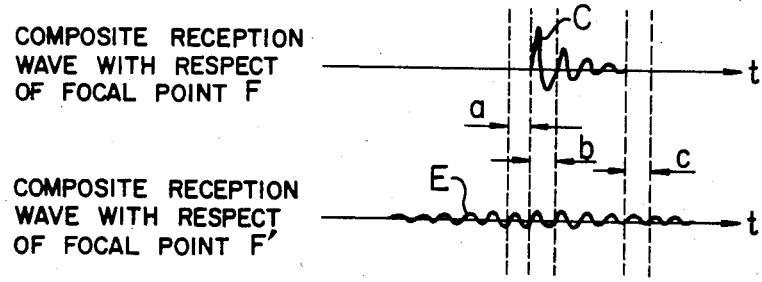
FIG. 7a is an explanatory diagram showing the principle of the present invention in which shown are the respective detection time bands of the composite reception waves in the relation between the composite reception wave in FIG. 5 and the composite reception wave in FIG. 6.
Figure 7B:
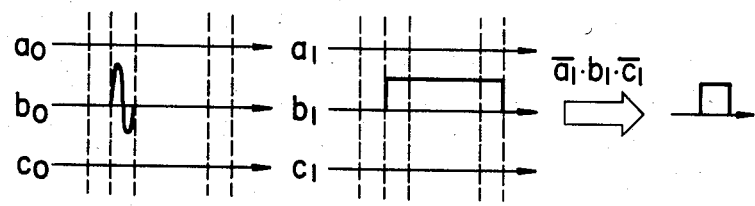
FIG. 7b is an explanatory diagram showing the principle of the present invention in which shown in left is the waveform in the respective time bands of the composite reception wave as shown in the upper portion in FIG. 7a, shown in center is a signal obtained as the result of inspection, and shown in right is a judgement computing resultant signal based on the result of inspection.
Figure 7C:
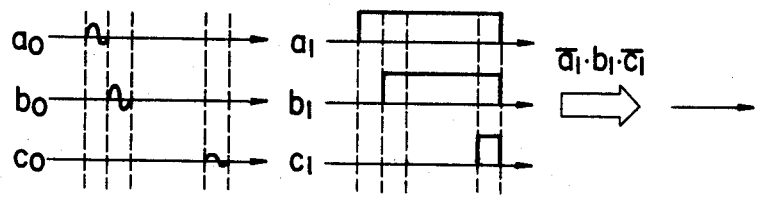
FIG. 7c is an explanatory diagram similar to FIG. 7a and showing the waveform in the respective time bands of the composite reception wave shown in the lower portion in FIG. 7a, a signal obtained as the result of inspection and a judgement computing resultant signal.
Figure 8:
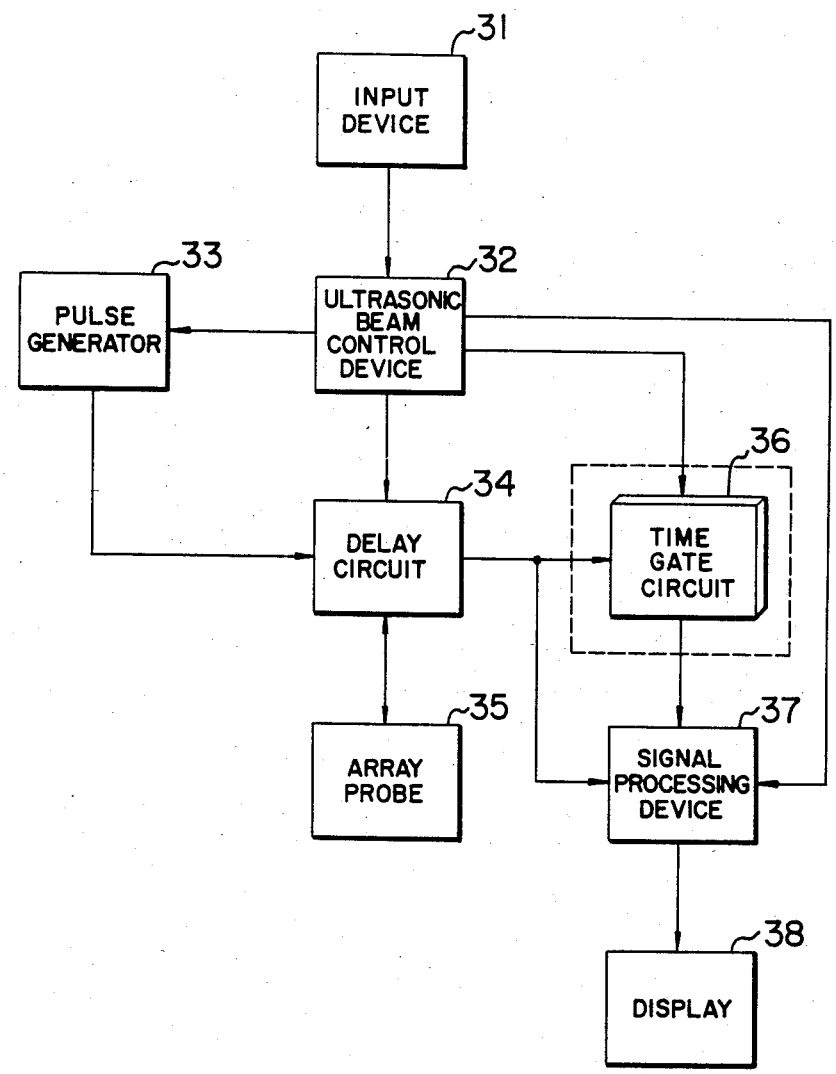
FIG. 8 is a schematic block diagram showing an embodiment of the ultrasonic inspection apparatus according to the present invention.
Figure 9:
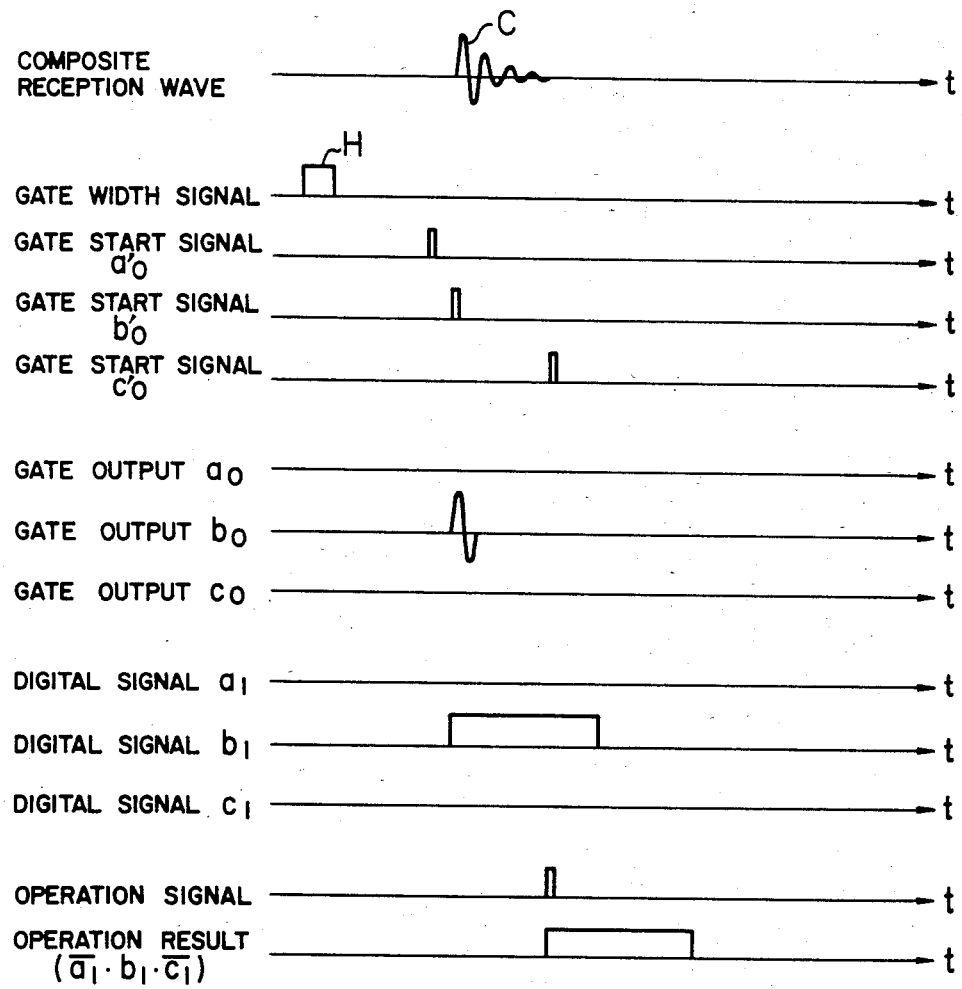
FIG. 9 is an explanatory diagram showing various signals in the time gate circuit of FIG. 8 with respect to the lapse of time as to the case of reception wave from the main lobe, according to an embodiment of the present invention.
Figure 10:
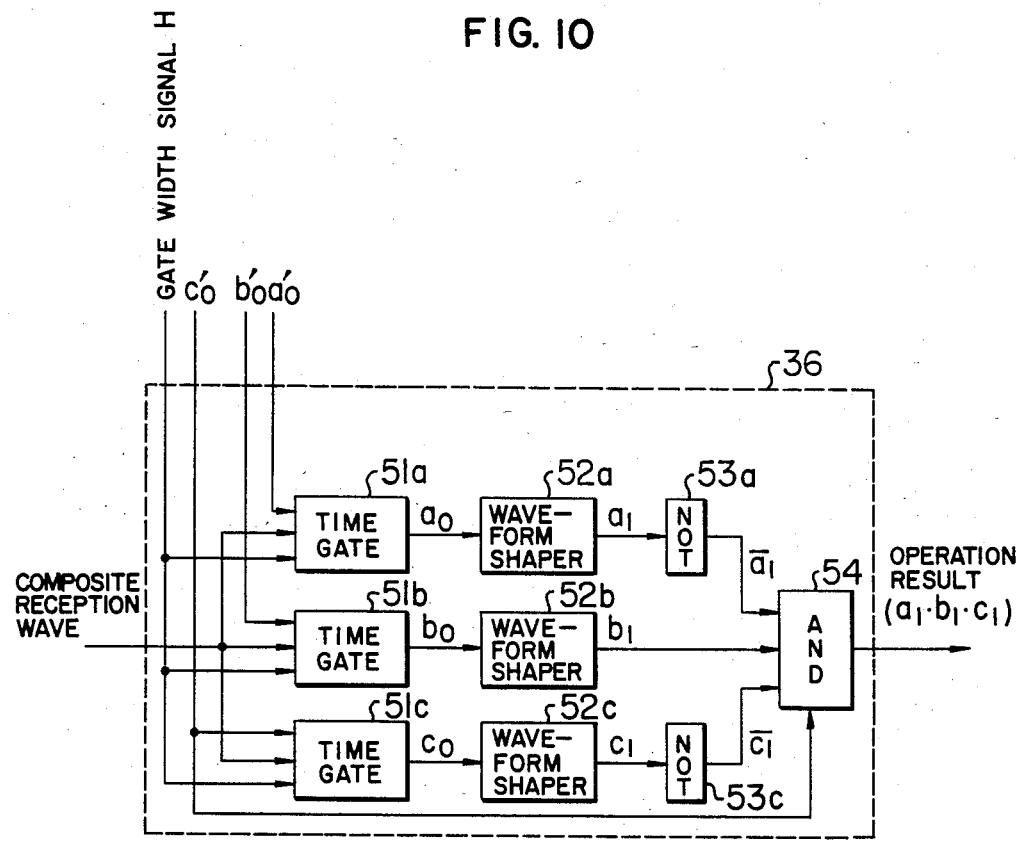
FIG. 10 is a block diagram showing the arrangement of the time gate circuit shown in FIG. 8 according to an embodiment of the present invention.

Prior to the description of an embodiment of the present invention by referring to FIGS. 8 to 10, the principle of the ultrasonic echo judgement according to the present invention is described. FIGS. 5, 6, 7a, 7b and 7c are diagrams for the explanation of the principle. Among these drawings, FIG. 5 shows that in what timing the ultrasonic waves are transmitted from the vibrator elements 3A to 3D of FIG. 4 and in what timing the ultrasonic echoes with respect to the transmitted ultrasonic waves are received from the focal point F when a reflector exists at the focal point F.

Figure 11:
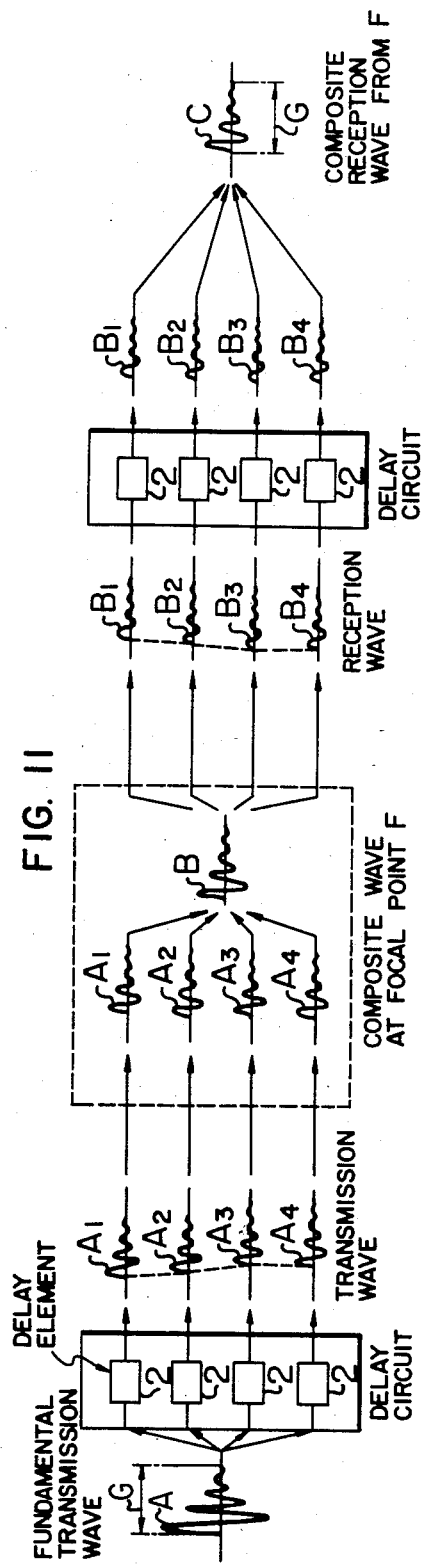
FIG. 11 is a diagram showing the state of signal waves in which the respective signal waves shown in FIG. 5 are illustrated in series.

In FIG. 5, although the ultrasonic waveform transmitted from each of the vibrator elements 3A to 3D is the fundamental transmission wave A as shown if a high tension impulse is directly applied to each vibrator element, a high tension impulse is applied to the respective vibrator elements through the corresponding delay elements in an actual case so that the impulse is transmitted as the transmission waves $A_1$, $A_2$, $A_3$ and $A_4$ from the respective vibrator elements. Thus, the transmission timings from the respective vibrator elements 3A to 3D are shifted in the manner as shown in FIGS. 5 and 11. The transmission timings are adjusted by the respective delay elements such that the transmission waves $A_1$, $A_2$, $A_3$ and $A_4$ can reach the focal point F at the same time and the respective phases of the transmission waves $A_1$, $A_2$, $A_3$ and $A_4$ coincide with each other, so that the composite wave B of the transmission waves $A_1$, $A_2$, $A_3$ and $A_4$ is as shown in FIG. 5. If a reflector exists at the focal point F, the composite wave B of the transmission waves $A_1$, $A_2$, $A_3$ and $A_4$ is reflected as reflection echoes toward the respective vibrator elements with the same phase and the same timing. The vibrator elements 3A to 3D receive this reflection echoes as the reception waves $B_1$, $B_2$, $B_3$ and $B_4$ after the lapse of time corresponding to the wave propagation distances from the focal point F to the respective vibrator elements 3A to 3D, so that the reception timings of the reception waves $B_1$, $B_2$, $B_3$ and $B_4$ become shifted from each other, as shown in FIGS. 5 and 11, by the time difference set in the respective delay elements. The reception waves $B_1$, $B_2$, $B_3$ and $B_4$ are converted by the respective vibrator elements 3A to 3D into electric signals which are passed through the respective delay elements to make the above-mentioned time difference vanish and added to each other to be composed into a reception composite wave C. Thus, the arrival timings of the respective transmission waves $A_1$, $A_2$, $A_3$ and $A_4$ coincide with each other, so that the duration of the composite signal B is the same as the duration G of the fundamental transmission wave A. The duration of each of the reception waves $B_1$, $B_2$, $B_3$ and $B_4$ also coincides with the duration of the fundamental transmission wave A. If such reception waves $B_1$, $B_2$, $B_3$ and $B_4$ are added to be composed with each other while they are registered with each other in timing at their respective left end in the drawing, the duration of the composite reception wave C obtained by the above-mentioned addition and composition substantially coincides with the duration G of the fundamental transmission wave A.

Figure 12:
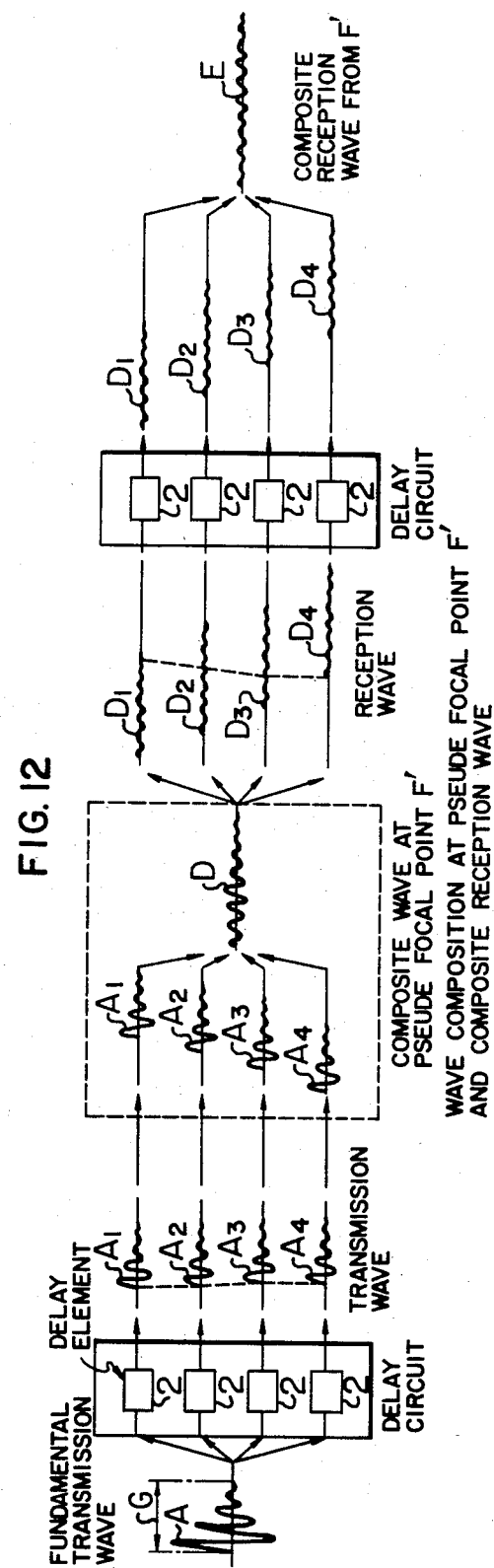
FIG. 12 is a diagram showing the state of signal waves in which the respective signal waves shown in FIG. 6 are illustrated in series.

FIGS. 6 and 12 similarly shows the various waveforms shown in FIGS. 5 and 11, with respect to the pseudo focal point F'. As seen in FIGS. 6 and 12, the duration of the composite wave D at the pseudo focal point F' of the respective transmission waves $A_1$, $A_2$, $A_3$ and $A_4$ is longer than the duration G of the fundamental transmission wave A. This is because the transmission ultrasonic wave from the vibrator element 3D first apears at the pseudo focal point F' and then the transmission ultrasonic waves from the vibrator elements 3C, 3B, and 3A successively appear at the pseudo focal point F' in above-named order, to thereby be composed thereat. Although ultrasonic echoes are reflected from a reflector toward the vibrator elements 3A to 3D if the reflector exists at the pseudo focal point F', the reflection timings do not coincide with each other and shift by an integer multiple from each other differing from the case of FIG. 5. As the result, the ultrasonic echoes reflected from the pseudo focal point F' and received by the vibrator elements 3A to 3D as the reception waves $D_1$, $D_2$, $D_3$ and $D_4$ are as shown in FIG. 6 and the duration of the addition/composite wave E is further elongated.

If a focal point F is determined in advance as a detection position, the respective timings at which the ultrasonic echoes are received by the vibrator elements are known at the time when the focal point is determined and the duration of the ultrasonic echoes are also known, so that if this fact is utilized, it is made possible to judge or determine whether the ultrasonic echoes are based on the main lobe or grating lobe when the ultrasonic echoes are obtained. FIGS. 7a, 7b, and 7c illustrate the way of judgement.

As shown in FIG. 7a, the duration of the composite reception wave C with respect to the focal point F is substantially the same as that of the transmission ultrasonic wave and therefore it is made possible to perform the judgement as to whether the ultrasonic echoes are those from the main lobe of ultrasonic beam or not on the basis of an ultrasonic signal extracted though a time gate having time width agreed with the period of the used ultrasonic wave. For the setting of the starting time of this time gate, it is preferable to use a delay circuit control signal used in an ultrasonic beam control device (32 in FIG. 8). For example, in the case the ultrasonic beam control device (32) performs the setting of the amount of delay time of a delay circuit (34 in FIG. 8) by a TTL level of a transistor-transistor-logic (TTL) (not shown) used is a circuit in which the TTL level signal (delay circuit control signal) is converted into an analog quantity of voltage by a D-A converter and a gate is opened when a comparator detects the fact that the analog quantity of voltage exceeds a predetermined voltage. However, it is not clear depending on the test piece whether the pseudo focal point F' in the grating lobe is generated in front of or in the rear of the focal point F of the main lobe in the sense of distance, and its becomes necessary to provide at least three time gates a, b and c, as shown in FIG. 7a, which are different from each other in their time gate starting time. That is, the gate starting time is set such that one of the three time gates abstracts the ultrasonic echoes from the focal point F, one of the remainder two time gates extracts the ultrasonic echoes reflected before the first-mentioned ultrasonic echoes, and the remainder time gate starts its time gating at the ending time of the duration of the ultrasonic echoes from the focal point F. The ultrasonic reception signals extracted through these at least three time gates a, b and c which are the gate outputs $a_0$, $b_0$ and $c_0$ are converted through waveform shapers such as comparators into digital signals $a_1$, $b_1$ and $c_1$ composed of "0" and "1" and subject to logic operations $\bar{a}_1$, $b_1$ and $\bar{c}_1$, as shown in FIGS. 6 and 7, so that it is made possible to judge whether the ultrasonic echoes obtained at the time point at which the ultrasonic echoes from the focal point F can be obtained is those from the focal point F or from the pseudo focal point F'.

The logic operations will be now explained here. Since each of the digital signals $a_1$, $b_1$ and $c_1$ can take, generally, either one of the two states, "0" and "1", the operations may include eight modes as shown in the following table.

TABLE

| Case No. | Signal States | | | Computing inputs | | | Results of Computing |
|---|---|---|---|---|---|---|---|
| | $a_1$ | $b_1$ | $c_1$ | $\bar{a}_1$ | $b_1$ | $\bar{c}_1$ | $\bar{a} \cdot b_1 \cdot \bar{c}_1$ |
| 1 | 0 | 0 | 0 | 1 | 0 | 1 | 0 |
| 2 | 0 | 0 | 1 | 1 | 0 | 0 | 0 |
| 3 | 0 | 1 | 0 | 1 | 1 | 1 | 1 |
| 4 | 0 | 1 | 1 | 1 | 1 | 0 | 0 |
| 5 | 1 | 0 | 0 | 0 | 0 | 1 | 0 |
| 6 | 1 | 0 | 1 | 0 | 0 | 0 | 0 |
| 7 | 1 | 1 | 0 | 0 | 1 | 1 | 0 |
| 8 | 1 | 1 | 1 | 0 | 1 | 0 | 0 |

As seen from the table shown above, it is possible to determine that a reflector exists at the focal position F in the third case where ultrasonic waves can be extrcted only by the time gate b. In any case other than the third case, it is determined that no ultrasonic waves can be obtained or that even if ultrasonic waves are obtained they are those from the pseudo focal point F'. Although a further method in which the judgement as to whether ultrasonic waves are those from the focal point F or not is made on the basis of the difference in amplitude of the reception ultrasonic waves may be considered, there are possibilities of occurrence of errors in this method in the case where the amplitude of the ultrasonic echoes from the main lobe of ultrasonic beam is smaller than that of the ultrasonic echoes from the grating lobe, and therefore the method according to the present invention is more effective than this method. Although the explanation has been made above by using a focused ultrasonic beam for the sake of simplification of description, it is a matter of course that the method of the invention can be applied to the case of a non-focused ultrasonic beam by suitably adjusting the time gate width of at least three time gate circuits and the relation of the point of time gate starting time of the three gate circuits.

Now, the ultrasonic transmission/reception apparatus according to the present invention will be described.

FIG. 8 shows the outline of arrangement of the apparatus. In this arrangement, an input device 31 serves to input control parameters such as the acoustic velocity in the test piece, the frequency of the used ultrasonic wave, the scanning region of the ultrasonic beam in the test piece, etc. which are applied to an ultrasonic beam control device 32. The ultrasonic beam control device 32 performs its control operation such that it transmits a pulse generation signal, a delay time control signal, a time gate start signal (including a time gate width signal), and flaw position signal to a pulse generator 33, a delay circuit 34, a time gate circuit 36, and a signal processing device 37, respectively, so that an ultrasonic beam is transmitted to a predetermined position in a test piece and an obtained reflection echo signal is displayed. The pulse generator 33 generates a high tension pulse (impulse or high-frequency pulse) for ultrasonic inspection in response to the pulse generation signal from the ultrasonic beam control device 32 and transmits the high tension pulse to the delay circuit 34. The delay circuit 34 supplies the high tension pulse from the pulse generator 33 to an array probe with time delays in response to the delay time control signal for vibrator elements of the array probe 35 from the ultrasonic beam control device 32. The array probe 35 transmits, on the basis of the time-delayed high tension pulses, ultrasonic beams under the control of deflection and focusing into a test piece. The thus transmitted ultrasonic waves propagates in the test piece and is reflected by a reflector if there exists any reflector in the test piece. The reflection ultrasonic waves are received by the array probe 35 and then supplied to a signal processing device 37 and a gate circuit 36 according to the present invention after composed through the delay circuit 34. In the time gate circuit 36, a necessary portion is extracted out of the reception ultrasonic waves in response to the time gate start signal and the time gate width signal from the ultrasonic beam control device 32 and the extracted ultrasonic signal portion is subject to logic operations in a predetermined way after it has been coded into a binary signal of "0" and "1" by a waveform shaper in the circuit 36, the result of logic operations being supplied to the signal processing device 37. Upon the reception of the result of logic operations, the signal processing device 37 obtains the position of the reflector by using an ultrasonic beam control signal, with respect to the incident angle of ultrasonic beam into the test piece, the focal position in the test piece, etc., applied from the ultrasonic beam control device 32, a reception ultrasonic signal from the delay circuit 34, and a reflection wave judgement signal representing the reflection ultrasonic wave from the main lobe of ultrasonic beam applied from the time gate circuit 36. The signal processing device 37 transmits data such as a reflector position signal, an ultrasonic scanning signal, etc., to the display 38. On the basis of the data from the signal processing device 37, the display 38 can display the shape of the reflector in the test piece on A, B and C scopes, the indication as to whether the reflection waves are those from the main lobe of the ultrasonic beam or not, or only the indication of the reflection waves from the main lobe.

The operation of the time gate circuit 36 will be described in detail hereunder. FIG. 9 is a time chart of various signals in the circuit 36. Upon the reception of a gate width signal H from the ultrasonic beam control device 32, the three gate circuits set their gate widths respectively corresponding to the gate width signal and wait for the respective gate start signals $a_0'$, $b_0'$ and $c_0'$. That is, the time (gate width) of the three gates 51a, 51b, and 51c is set on the basis of the gate width signal and the time gates 51a, 51b, and 51c wait for the gate start signals $a_0'$, $b_0'$ and $c_0'$. The gate width signal H is inputted in advance into the input device 31 as one wavelength time of the ultrasonic wave. Since the gate start time varies depending on the kind of array probe used, the gate start time is once inputted into the input device 31 and made to agree with the reception of ultrasonic wave by using a computing circuit or computer in the ultrasonic beam control device 32 to thereby transmit the signals $a_0'$, $b_0'$ and $c_0'$. When the gate start signals $a_0'$, $b_0'$ and $c_0'$ are received from the ultrasonic beam control device 32, the composite signal C is subject to the time gates a, b and c so that the composite signal portions are extracted at the respective time gates a, b and c as the gate outputs $a_0$, $b_0$ and $c_0$. These gate outputs $a_0$, $b_0$ and $c_0$ are converted into the digital signals $a_1$, $b_1$ and $c_1$ of "0" and "1" which are outputted and held as they are until the gate time band of the time gate c terminates. Then, logic operation ($\bar{a}_1 \cdot b_1 \cdot \bar{c}_1$) is made among the digital signals $a_1$, $b_1$ and $c_1$ by using the time gate start signal $c_0'$ in response to an operation start signal, so that it is possible to detect whether the reception composite wave is based on the ultrasonic echoes from the main lobe of the ultrasonic beam or not. FIG. 9 is a time chart in the case where the ultrasonic echoes are those from the main lobe of the ultrasonic beam.

Referring to FIG. 10, the outline of the arrangement of the time gate circuit 36 performing the operation described above will be described here. In this arrangement, the gate circuits 51a, 51b and 51c corresponding to the time gates a, b and c are supplied with a common composite reception wave as well as the corresponding gate start signals $a_0'$, $b_0'$ and $c_0'$. The respective gate outputs $a_0$, $b_0$ and $c_0$ from the gate circuits 51a, 51b and 51c are converted into the digital signals $a_1$, $b_1$ and $c_1$ through waveform shaping circuits 52a, 52b, and 52c, which are constituted by such as comparators having variable sensitivity-adjusting-threshold value so as to have flip-flop functions, and then processed to gain a logical product by an AND circuit 54 in response to the gate start signal $c_0'$. Invertors, e.g., not circuits 53a and 53c are provided for inverting the digital signals $a_1$ and $c_1$. By using the signal representing the result of the above-mentioned logic operations, judgement is made as to whether the reflection echo image be displayed on the display 38 or not. That is, the input gate of the display 38 is closed when this signal is "0", while opened when this signal is "1".

As described above, according to the present invention, the existence of ultrasonic echoes is detected at a time point at which ultrasonic echoes can be obtained and time points in advance of and in the behind of the first mentioned time point, and when the existence is detected in a predetermined manner, the ultrasonic echoes are received as those from the main lobe. According to the present invention, therefore, there are advantages that the operations can be easily achieved, the arrangement is simple, and the position evaluation of a reflector existing in a test piece can be surely attained with a good S/N without being affected by the grating lobe.

We claim:

1. An ultrasonic inspection method in which ultrasonic waves respectively transmitted from a plurality of vibrator means are reflected by a reflector in a test piece of produce reflection waves and said reflection waves are received as reception signals composed into a composite signal, said method comprising the steps of:

detecting a first composite signal based on the reflection waves from a focal point in a main lobe at a first time point at which said first composite signal can be detected;

detecting a second composite signal based on the reflection waves from a pseudo focal point in said main lobe at a second time point in advance of said first time point;

detecting a third composite signal based on the reflection waves from said pseudo focal point in said main lobe at a third time point which is later than said first time point; and deciding that the first composite signal is based on the reflection waves from a position of an inspection target when only said first composite signal is detected.

2. An ultrasonic inspection apparatus having a plurality of vibrator means, composing means for receiving respective output signals of said plurality of vibrator means to compose said output signals to thereby produce a composite output, signal processing means for receiving said composite output of said composite means to thereby output processed signals to display means, said apparatus comprising:

a time gate circuit having a plurality of detection means which are arranged to receive said composite output of said composite means, detecting operation time points of said detection means being set to a first time point at which a first composite signal based on the reflection waves from a focal point in a main lobe can be detected and at least a second time point at which at least a second composite signal based on the reflection waves from a pseudo focal point in said main lobe can be detected, and a judgement circuit connected to the respective outputs of said plurality of detection means and for judging a state in which only said first composite signal is detected.

3. An ultrasonic inspection apparatus according to claim 2, in which the output of said judgement circuit is connected to the input of said signal processing means.

4. An ultrasonic inspection apparatus according to claim 2, in which said detection means comprises at least one first gate means which is arranged such that the timing at which an input signal to said first gate means is allowed to pass therethrough is set to agree with the timing at which at least a part of the first composite signal based on the reflection waves from said focal point in said main lobe is allowed to pass therethrough and at least a second and a third gate means which are arranged such that the timing at which an input signal to each of said second and third gate means is allowed to pass therethrough is set to disagree with the timing at which the first composite signal based on the reflection waves from said focal point in said main lobe is allowed to pass therethrough.

5. An ultrasonic inspection apparatus according to claim 4, in which said judgement circuit is a logic-circuit wherein an AND gate having a first input connected to the output of said first gate means through a first waveform shaper and a second and a third input connected to the respective outputs of said second and third gates means through a second and a third waveform shaper and a first and a second invertor respectively.

6. An ultrasonic inspection apparatus according to claim 2, in which said time gate circuit comprises:

a first gate means arranged to receive the first composite signal and to be actuated in response to a gate start signal of said first time point at which the first composite signal based on the reflection waves from said focal point in said main lobe can be detected;

a second gate means arranged to receive the second composite signal and to be actuated at said second time point which is in advance of said first time point;

a third gate means arranged to receive the second composite signal and to be actuated at a third time point which is later than said first time point;

a first waveform shaper arranged to receive a signal allowed to pass through said first gate means;

a second waveform shaper arranged to receive a signal allowed to pass through said second gate means;

a third wavefrom shaper arranged to receive a signal allowed to pass through said third gate means;

a first inverter arranged to receive an output of said second waveform shaper;

a second inverter arranged to receive an output of said third waveform shaper; and AND gate means arranged to receive an output of said first waveform shaper, an output of said first inverter, and an output of said second inverter.

* * * * *